US007179813B2

(12) United States Patent
Kelly et al.

(10) Patent No.: US 7,179,813 B2
(45) Date of Patent: Feb. 20, 2007

(54) BICYCLIC INDOLYL DERIVATIVES AND METHODS FOR THEIR USE AS SEROTONERGIC AGENTS

(75) Inventors: Michael G. Kelly, Thousand Oaks, CA (US); Wayne E. Childers, New Hope, PA (US); Boyd L. Harrison, Princeton Junction, NJ (US); Gan Zhang, Niwot, CO (US); Byron A. Bravo, Eagleville, PA (US); Lee E. Schechter, Toms River, NJ (US)

(73) Assignee: Wyeth, Madison, NJ (US)

( * ) Notice: Subject to any disclaimer, the term of this patent is extended or adjusted under 35 U.S.C. 154(b) by 167 days.

(21) Appl. No.: 10/864,698

(22) Filed: Jun. 9, 2004

(65) Prior Publication Data

US 2005/0124630 A1 Jun. 9, 2005

Related U.S. Application Data

(60) Provisional application No. 60/477,575, filed on Jun. 11, 2003.

(51) Int. Cl.
*A61K 31/496* (2006.01)
*C07D 401/14* (2006.01)
(52) U.S. Cl. .................................. 514/253.09; 544/364
(58) Field of Classification Search ...................... None
See application file for complete search history.

(56) References Cited

U.S. PATENT DOCUMENTS 5,723,464 A    3/1998   Brightwell et al. .......... 514/254

FOREIGN PATENT DOCUMENTS

| EP | 0 372 657 A1 | 6/1990 |
| EP | 0 395 312 A2 | 10/1990 |
| EP | 0 512 755 A2 | 11/1992 |
| EP | 0 737 678 A1 | 10/1996 |
| WO | WO 95/33743 A1 | 12/1995 |

OTHER PUBLICATIONS

Jones et al, Pharmacology, Biochemistry and Behavior, vol. 71, p. 555-568 (2002).*
Schechter et al. Current Pharmaceutical Design, vol. 8, p. 139-145 (2002).*
Patat et al. Clinical Pharmacology & Therapeutics, vol. 77, p. P29. (2005).*
Pedigo et al., "Discrimation of Multiple [3H]5-Hydroxytryptamine Binding Sites by the Neuroleptic Spiperone in Rat Brain," *J. Neurochem.* 1981, 36, 220.
Fargin et al., "The genomic clone G-21 which resembles a β-adrenergic receptor sequence encodes the 5-$HT_{1A}$ receptor," *Nature* 1988, 335, 358.
K. Rasmussen and V. P. Rocco, "Recent Progress in Serotonin (5-HT)$_{1A}$ Receptor Modulators," *Annual Reports in Medicinal Chemistry*, vol. 30, J. A. Bristol, ed., 1-9 (1995).

L. E. Schechter and M. G. Kelly, "An Overview of 5-$HT_{1A}$ Receptor Antagonists: Historical Perspective and Therapeutic Targets," *Current Drugs Serotonin ID Research Alert* 1997, 2, 299-309.
Bundgaard, et al., *Journal of Drug Delivery Reviews* 1992, 8, 1-38.
D. J. Bill and A. Fletcher, "Correlation of in vivo functional and anxiolytic effects of 5-$HT_{1A}$ receptor ligands in the mouse," *Br. J. Pharmacol.* 1994, 111, 151P.
Krogsgaard-Larsen, et al., (ed.), *Design and Application of Prodrugs, Textbook of Drug Design and Development*, Chapter 5, 113-191 (1991).
Bundgaard, "Glycolamide Esters as Biolabile Prodrugs of Carboxylic Acid Agents: Synthesis, Stability, Bioconversion, and Physicochemical Properties," *Journal of Pharmaceutical Sciences* 1988, 77, 285.
J-L. Moreau, et al., "Behavioral Profile of the 5-$HT_{1A}$ Receptor Antagonist (S)-UH-301 in Rodents and Monkeys," *Brain Res. Bull.* 1992, 29, 901.
R. J. Rodgers and J. C. Cole, "Anxiolytic-like effect of (S)-WAY 100135, a 5-$HT_{1A}$ receptor antagonist, in the murine elevated plus-maze test," *Eur. J. Pharmacol.* 1994, 261, 321-325.
J. F. Deakin, et al., "Clinical implication of microdialysis findings," *Trends Pharmacol. Sci.*, 1993, 14, 263.
S. Hjorth and S. B. Auerbach, 5-$HT_{1A}$ autoreceptors and the mode of action of selective serotonin reuptake inhibitors (SSRI), *Behav. Brain Res.* 1996, 73, 281-283.
Schechter et al., "Serotonergic antidepressants: Current and future perspectives," *Current Opinion in CPNS Investigational Drugs* 1999, 1, 432-447.
T. Hashimoto, et al., "Increase in serotonin 5-$HT_{1A}$ receptors in prefrontal and temporal cortices of brains from patients with chronic schizophrenia," *Life Sci.*, 1991, 48, 355-363.
J. N. Joyce, et al., "Serotonin Uptake Sites and Serotonin Receptors Are Altered in the Limbic System of Schizophrenics," *Neuropsychopharmacol.* 1993, 8, 315-336.
P. W. J. Burnet, et al., "5-$HT_{1A}$ and 5-$HT_{2A}$ Receptor mRNAs and Binding Site Densities Are Differentially Altered in Schizophrenia," *Neuropsychopharmacol.*, 1996, 15(5), 442-455.
H. Y. Meltzer, "Role of Serotonin in the Action of Atypical Antipsychotic Drugs," *Clin. Neurosci.* 1995, 3, 64-75.
M. Hamon, et al., "Alterations of Central Serotonin and Dopamine Turnover in Rats Treated with Isapirone and Other 5-Hydroxytryptamine$_{1A}$ Agonists with Potential Anxiolytic Properties," *J. Pharmacol. Exp. Ther.* 1988, 246(2), 745-752.
L. E. Schechter, et al., "Alterations of Central Serotoninergic and Dopaminergic Neurotransmission in Rats Chronically Treated with Ipsapirone: Biochemical and Electrophysiological Studies," *J. Pharmacol. Exp. Ther.* 1990, 255, 1335-1347.

(Continued)

*Primary Examiner*—Emily Bernhardt
(74) *Attorney, Agent, or Firm*—Woodcock Washburn LLP

(57) ABSTRACT

Bicyclic indolyl derivatives and compositions containing such compounds are disclosed. Methods of using the bicyclic indolyl derivatives and compositions containing such composition as serotonergic agents, such as in the treatment of depression and anxiety, are also disclosed. In addition, processes for the preparation of bicyclic indolyl derivatives are disclosed.

14 Claims, No Drawings

OTHER PUBLICATIONS

K. Q. Do, et al., γ-Glutamylglutamine and Taurine Concentrations Are Decreased in the Cerebrospinal Fluid of Drug-Naïve Patients with Schizophrenic Disorders, *J. Neurochem.* 1995, 65, 2652-2662.

G. C. Tsai, et al., "Abnormal Excitatory Neurotransmitter Metabolism in Schizophrenic Brains," *Arch. Gen. Psychiatry* 1995, 52, 829-36.

Schechter et al., "The Potential Utility of 5-HT$_{1A}$ Receptor Antagonists in the Treatment of Cognitive Dysfunction Associated with Alzheimer's Disease," *Current Pharmaceutical Design* 2002, 8, 139-145.

Harder et al., The 5-HT$_{1A}$ antagonist, WAY 100635, ameliorates the cognitive impairment induced by fornix transaction in the marmoset, *Psychopharmacol.* 1996, 127, 245-254.

Carli et al, "(S)-WAY 100135, a 5-HT$_{1A}$ receptor antagonist, prevents the impairment of spatial learning caused by intrahippocampal scopolamine," *Eur. J. Pharmacol.* 1995, 283, 133-139.

Harder et al., "The 5-HT$_{1A}$ antagonist, WAY 100 635, alleviates cognitive impairments induced by dizocilpine (MK-801) in monkeys," *Neuropharmacology*, 2002, 39, 547-552.

P. T. Francis, et al., *Neurotransmitters and Neuropeptides in Alzheimer's Disease*, R. D. Terry, ed., Raven Press, Ltd., New York, 247-261 (1994).

U. Staubli, et al., "Facilitation of glutamate receptors enhances memory," *PNAS* (USA) 1994, 91, 777-781.

R. G. Morris, et al., "Selective impairment of learning and blockade of long-term potentiation by an N-methyl-D-aspartate receptor antagonist," *Nature* 1986, 319, 774-776.

T. V. Bliss and G. L. Collinridge, "A synaptic model of memory: long-term potentiation in the hippocampus," *Nature* 1993, 361, 31-39.

J. T. Greenmyre, "The Role of Glutamate in Neurotransmission and in Neurologic Disease," *Arch. Neurol.* 1986, 43, 1058-1063.

W. F. Maragos, et al., "Glutamate dysfunction in Alzheimer's disease: an hypothesis," *Trends Neurosci.* 1987, 10, 65-8.

B. T. Hyman, et al., "Alzheimers's Disease: Glutamate Depletion in the Hippocampal Perforant Pathway Zone," *Ann. Neurol.* 1987, 22, 37-40.

N. W. Kowall and M. F. Beal, Glutamate-, Glutaminase-, and Taurine- immunreactive Neurons Develop Neurofibrillary Tangles in Alzheimer's Disease, *Ann. Neurol.* 1991, 29, 162-167.

D. M. Bowen, et al., Neurotransmission—the link integrating Alzheimer research? *Trends Neurosci.* 1994, 17, 149-150.

S. N, Dijk, et al., "NMDA-induced glutamate and aspartate release from rat cortical pyramidal neurons: evidence for modulation by a 5-HT$_{1A}$ antagonist," *Br. J. Pharmacol.* 1995, 115, 1169-74.

R. Araneda and R. Andrade, "5-Hydroxytryptamine$_2$ and 5-Hydroxytryptamine$_{1A}$ receptors mediate opposing responses on membrane excitability in rat association cortex," *Neuroscience* 1991, 40, 399-412.

D. M. McLoughlin, et al., "Central Serotonergic Hyperresponsivity in Late-Onset Alzheimer's Disease," *Am. J. Psychiatry* 1994, 151, 1701-3.

J. D. Buxbaum, et al., "Protein phosphorylation inhibits production of Alzheimer amyloid β /A4 peptide," *PNAS* (USA), 1993, 90, 9195-8.

N. Sakai and C. Tanaka, "Inhibitory modulation of long-term potentiation via the 5-HT$_{1A}$ receptor in slices of the rat hippocampal dentate gyrus," *Brain Res.* 1993, 613, 326-30.

K. Briner and R. C. Dodel, "New Approaches to Rapid Onset Antidepressants," *Cur. Pharm. Des.* 1998, 4(4), 291-302 plus Erratum.

M. B. Tome, et al., "Paroxetine and pindolol: a randomized trial of serotonergic autorecptor blockade in the reduction of antidepressant latency," *Int. Clin. Psy.* 1997, 12, 81-9.

V. Perez, et al., Randomised, double-blind, placebo-controlled trial of pindalol in combination with fluoxetine antidepressant treatment, *Lancet* 1997, 349, 1594-7.

P. A. Abrahamsson, et al., "Peptide-Hormone- and Serotonin-Immunoreactive Cells in Normal and Hyperplastic Prostate Glands," *Pathol. Res. Pract.* 1986, 181, 675-683.

N. M. Hoosein, et al., Expression of Neuroendocrine Factors and Extracellular Matrix Degradative Enzymes in Human Prostate Tumor Cells, *J. Urol.* 1993, 149, p. 479A. Abstract No. 1066.

M. Abdul, et al., Growth Inhibition of Human Prostatic Carcinoma Cell Lines by Serotonin Antagonists, *Anticancer Res.* 1994, 14, 1215-20.

J. R. Hughes and D. Hatsukami, "Signs and Symptoms of Tobacco Withdrawal," *Arch. Gen. Psychiatry* 1986, 43, 289-94.

K. Rasmussen and J. F. Czachura, Nicotine withdrawal leads to increased sensitivity of serotonergic neurons to the 5-HT$_{1A}$ agonist 8-OH-DPAT, *Psychopharmacology* 1997, 133, 343-6.

D. R. Helton, et al., "Nicotine withdrawal: a behavioral assessment using schedule controlled responding, locomotor activity, and sensorimotor reactivity," *Psychopharmacology* 1993, 113, 205-10.

K. Rasmussen, et al., "Serotonin-1A Antagonists Attenuate the Effects of Nicotine Withdrawal on the Auditory Startle Response," *Synapse* 1997, 27, 145-52.

K. Rasmussen, et al., "The Novel 5-Hydroxytryptamine$_{1A}$ Antagonist LY426965: Effects on Nicotine Withdrawal and Interactions with Fluoxetine," *J. Pharmacol. Exp. Ther.* 2000, 294(2), 688-700.

Kenny et al., "Anxiogenic effects of nicotine in the dorsal hippocampus are mediated by 5-HT$_{1A}$ and not by muscarinic M$_1$ receptors," *Neuropharmacology* 2000, 39, 300-7.

Cheeta, "The dorsal raphé nucleus is a crucial structure mediating nicotine's anxiolytic effects and the development of tolerance and withdrawal responses," *Psychopharmacology* 2001, 155, 78-85.

File et al., Neurobiological mechanisms by which nicotine mediates different types of anxiety, *Eur. J. Pharmacol.* 2000, 393, 231-6.

Sharma et al., "Distribution of the 5-Hydroxytryptamine$_{2C}$ Receptor Protein in Adult Rat Brain and Spinal Cord Determined Using a Receptor-Directed Antibody," *Synapse* 1997, 27, 45-56.

Obach et al., "Inhibition of Human Cytochrome P450 Enzymes aby Constituents of St. John's Wort, an Herbal Preparation Used in the Treatment of Depression," *J, Pharmacol. Exp. Ther.* 2000, 294, 88-95.

Tichy et al., "Stereochemical Studies. LV. Evaluation of Some 1,3-*syn*-Axial Interactions in Six-membered Ring Systems," *Coll. Czech. Chem. Commun.* 1970, 35, 459-68.

Boehme et al., "Stereochemistry of Diels-Alder Adducts. II. The Alkylation of Some Bicyclic Nitriles," *J. Am. Chem. Soc.* 1958, 80, 5488-95.

Christol et al., "H and C NMR Study of the Effects Exerted by an Oxirane Ring in the Epoxybicyclo-[2.2.2.]octane Series," *Org. Magn. Res.* 1981, 17, 110-117.

Hansen et al., "An Enantioselective Synthesis of Cis Perhydroisoquinoline LY235959," *J. Org. Chem.* 1998, 63, 775-85 (plus 12 pages supporting information).

Stapersma nad Klumpp, "7-Lithio-Norbornadiene," *Tetrahedron* 1981, 37, 187-9.

Freeman and Hutchinson, "Organolithium Reagents From Alkyl Halides and Lithium DI-*tert*-butylbiphenyl," *Tet. Lett.* 1976, 1849-52.

Kwart et al., "Isomerism in the Diels-Alder Reaction. III. The Bromination of the Diels-Alder Adduct, Norbornylene," *J. Am. Chem. Soc.* 1954, 76, 4072-7.

Moriarty, R. M. et al., "Structures of the γ-Lactones from the Acid-Catalyzed Cyclization of exo- and endo-2-Methylnorbornene-2-carboxylic acid," *J. Org. Chem.* 1979, 44, 2206-10.

Gopal et al., "Ruthenium Tetroxide Oxidation in Neutral and Basic Media," *Tetrahedron* 1972, 28, 4259-66.

Dunlop et al., "Characterization of 5-HT$_{1A}$ Receptor Functional Coupling in Cells Expressing the Human 5-HT$_{1A}$ Receptor Functional Coupling in Cells Expressing the Human 5-HT$_{1A}$ Receptor as Assessed with the Cytosensor Microphysiometer," *J. Pharmacol. Toxicol. Methods* 1998, 40, 47-55.

Houle et al., "Imaging 5-HT$_{1A}$ receptors with positron emission tomography: Initial human studies with [$^{11}$C]CPC-222," *Nucl. Med. Commun.* (1997), 18:1130-1134.

Wilson, A. A. et al., "Derivatives of WAY 100635 as Potential Imaging Agents for 5-HT$_{1A}$ Receptors: Syntheses, Radiosyntheses, and in Vitro and in Vivo Evaluation," Nucl. Med. Biol. (1998) 25:769-776.

*Remington's Pharmaceutical Sciences*, 17th Ed., Gennaro, A. R. (Ed.), Mack Publishing Company, Easton, PA (1985) pp. 1409-1677.

Bundgaard, H. (ed.), *Design of Prodrugs*, Elsevier (1985), Ch. 1 (pp. 1-92), Ch. 4 (pp. 157-176), Ch. 5 (pp. 177-198), and Ch. 6 (pp. 199-241).

Widder, et al. (ed.), *Methods in Enzymology*, vol. 112, Academic Press (1985), pp. 309-323.

Higuchi and Stella (eds.), *Prodrugs as Novel Drug Delivery Systems*, American Chemical Society (1975), pp. 1-115 and 196-223.

Greene, T.W. and Wuts, P.G.M., *Protective Groups in Organic Synthesis* 2d. Ed., Wiley & Sons, 1991, Ch. 2 (pp. 10-142), Ch. 5 (pp. 224-276), and Ch. 7 (pp. 309-405).

* cited by examiner

BICYCLIC INDOLYL DERIVATIVES AND METHODS FOR THEIR USE AS SEROTONERGIC AGENTS

CROSS REFERENCE TO RELATED APPLICATIONS

This application claims the benefit of U.S. Application No. 60/477,575, filed Jun. 11, 2003, the entire disclosure of which is incorporated herein by reference.

FIELD OF THE INVENTION

This invention relates to novel piperazine derivatives, pharmaceutical compositions containing them and methods for their use. More specifically, the invention relates to novel bicyclic indolyl derivatives that are serotonergic agents.

BACKGROUND OF THE INVENTION

Much information concerning the serotonin 5-$HT_{1A}$ receptor subtype has been generated since its discovery in 1981 (Pedigo et al., *J. Neurochem.* 1981, 36, 220) and subsequent cloning in 1988 (Fargin et al., *Nature* 1988, 335, 358). Numerous preclinical studies suggest the potential usefulness of 5-$HT_{1A}$ antagonists in the treatment of various diseases and disorders of the central nervous system (CNS), particularly anxiety and depression. Preclinical and clinical data now indicate that compounds that antagonize 5-$HT_{1A}$ receptors may find use in the treatment, prevention and amelioration of central nervous system diseases and disorders, including anxiety, depression, schizophrenia and cognitive deficits resulting from neurodegenerative disorders like Alzheimer's disease; the enhancement of antidepressant activity; the treatment and amelioration of prostate cancer; and the treatment for smoking cessation and nicotine withdrawal. K. Rasmussen and V. P. Rocco, "Recent Progress in Serotonin (5-HT)$_{1A}$ Receptor Modulators," *Annual Reports in Medicinal Chemistry*, Volume 30, J. A. Bristol, ed., 1–9 (1995); L. E. Schechter and M. G. Kelly, "An Overview of 5-$HT_{1A}$ Receptor Antagonists: Historical Perspective and Therapeutic Targets," *Current Drugs Serotonin ID Research Alert* 1997, 2, 299–309.

Because antagonists of 5-$HT_{1A}$ receptors are expected to be useful in the treatment, prevention and amelioration of central nervous system diseases, the enhancement of antidepressant activity, the treatment and amelioration of prostate cancer, and the treatment for smoking cessation and nicotine withdrawal, it would be desirable to develop new compounds that are capable of binding to 5-$HT_{1A}$ receptors and antagonizing their activity. The novel bicyclic indolyl derivatives of this invention are serotonergic agents that antagonize 5-$HT_{1A}$ receptors and thus are expected to be beneficial in these and other important uses.

SUMMARY OF THE INVENTION

The present invention provides bicyclic indolyl derivatives that find use as serotonergic agents.

In one embodiment, the invention is directed to compounds of formula (I):

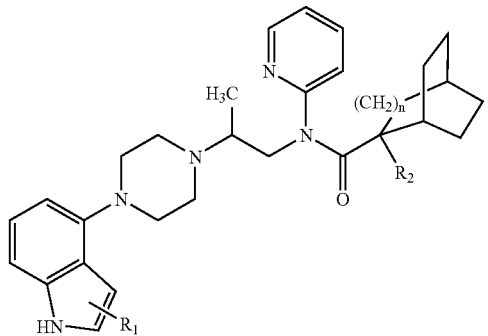

or a prodrug, stereoisomer, N-oxide or pharmaceutically-acceptable salt thereof;

wherein:

$R_1$ is H, halo or alkyl;

$R_2$ is H or lower alkyl; and n is 0 or 1.

In another embodiment, the invention is directed to compositions, comprising the compound of formula (I); and one or more pharmaceutically-acceptable carriers.

The novel compounds of formula (I) preferably bind with 5-$HT_{1A}$ and, in certain embodiments, are serotonin 5-$HT_{1A}$ antagonists, and as such are useful in treating, preventing or ameliorating several diseases and disorders associated with the binding and/or antagonism of 5-$HT_{1A}$ receptors, including the treatment, prevention and amelioration of central nervous system diseases and disorders, including anxiety, depression, schizophrenia and cognitive deficits resulting from neurodegenerative disorders like Alzheimer's disease; and the treatment and amelioration of prostate cancer. They are also useful as co-administered therapeutic agents to enhance the onset or potency of the antidepressant action of selective serotonin reuptake inhibitors (SSRI's) and for smoking cessation and relief of the symptoms resulting from nicotine withdrawal.

DETAILED DESCRIPTION OF THE INVENTION

In one aspect, the invention is directed to compounds of formula (I):

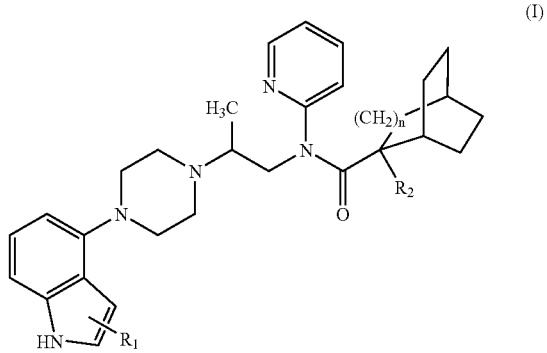

or a prodrug, stereoisomer, N-oxide or pharmaceutically-acceptable salt thereof;

wherein:
R₁ is H, halo or alkyl;
R₂ is H or lower alkyl; and
n is 0 or 1.

$R_1$ is preferably H or alkyl, more preferably H or lower alkyl, most preferably H. $R_2$ is preferably H or methyl, more preferably H. The symbol n is preferably 1. In certain preferred embodiments, $R_1$ is H or alkyl; $R_2$ is H or methyl; and n is 1. Combinations of such preferred meanings may be used.

Especially preferred examples of the compounds of the invention are the two diastereomeric isomers of formula (I):

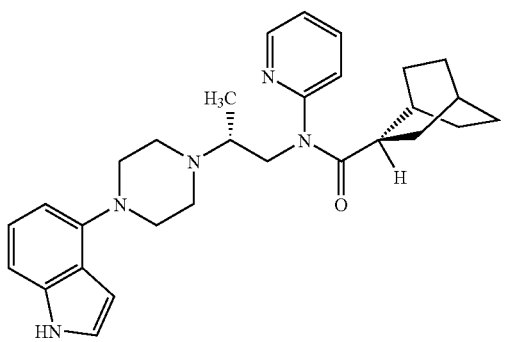

(Ia)

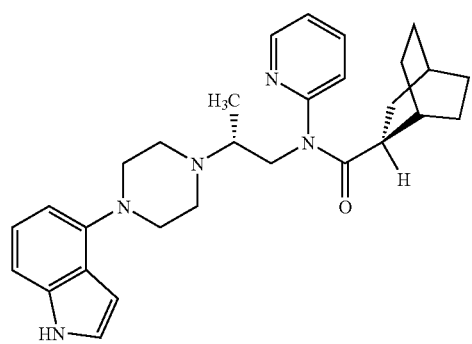

(Ib)

(S)-N-{(2R)-2-[4-(1H-indol-4-yl)piperazin-1-yl]propyl}-N-pyridin-2-ylbicyclo[2.2.2]octane-2-carboxamide [Formula (Ia)]; and (R)-N-{(2R)-2-[4-(1H-indol-4-yl)piperazin-1-yl]propyl}-N-pyridin-2-ylbicyclo[2.2.2]octane-2-carboxamide [Formula (Ib)];

or prodrug, N-oxide or pharmaceutically-acceptable salt thereof. The invention also includes N-{(2R)-2-[4-(1H-indol-4-yl)piperazin-1-yl]propyl}-7-methyl-N-pyridin-2-yl-bicyclo[2.2.1]heptane-7-carboxamide; N-{(2R)-2-[4-(1H-indol-4-yl)piperazin-1-yl]propyl}-7-methyl-N-pyridin-2-yl-bicyclo[2.2.1]heptane-7-carboxamide; or a prodrug, N-oxide or pharmaceutically-acceptable salt thereof.

The term "alkyl", as used herein, whether used alone or as part of another group, refers to a substituted or unsubstituted aliphatic hydrocarbon chain and includes, but is not limited to, straight and branched chains containing from 1 to 12 carbon atoms, preferably 1 to 6 carbon atoms, more preferably 1 to 4 carbon atoms, and most preferably one carbon atom, unless explicitly specified otherwise. For example, methyl, ethyl, propyl, isopropyl, butyl, i-butyl and t-butyl are encompassed by the term "alkyl." Specifically included within the definition of "alkyl" are those aliphatic hydrocarbon chains that are optionally substituted. Suitable substitutions include halo, with fluoro being particularly preferred. When the term "lower alkyl" is used herein, it refers to an alkyl, as defined above, containing 1 to 6 carbon atoms, preferably 1 to 4 carbons, and more preferably one carbon.

The carbon number as used in the definitions herein refers to carbon backbone and carbon branching, but does not include carbon atoms of the substituents, such as alkoxy substitutions and the like.

The term "halo" as used herein, refers to chloro, bromo, fluoro, or iodo.

When any variable occurs more than one time in any constituent or in any formula, its definition in each occurrence is independent of its definition at every other occurrence. Combinations of substituents and/or variables are permissible only if such combinations result in stable compounds.

The compounds employed in the methods of the present invention may exist in prodrug form. The term "prodrug," as used herein, refers to compounds specifically designed to maximize the amount of active species that reaches the desired site of reaction which are of themselves typically inactive or minimally active for the activity desired, but through biotransformation are converted into biologically active metabolites. Typically, prodrugs are covalently bonded carriers that release the active parent drug, for example, as according to formula (I), employed in the methods of the present invention in vivo when such prodrug is administered to a mammalian subject.

The term "stereoisomers," as used herein, refers to compounds that have identical chemical constitution, but differ as regards the arrangement of the atoms or groups in space. It is understood that compounds according to formula (I) may include one or more asymmetric carbons, and that formula (I) encompasses all possible stereoisomers and mixtures thereof, as well as racemic modifications, particularly those that possess the activities discussed herein. Compounds employed in the present methods may be isolated in optically active or racemic forms. Thus, all chiral, diastereomeric, racemic forms and all geometric isomeric forms of a structure are intended, unless the specific stereochemistry or isomeric form is specifically indicated. Stereoisomers of the compounds of formula (I) can be selectively synthesized or separated in pure, optically-active form using conventional procedures known to those skilled in the art of organic synthesis. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

The term "N-oxide," as used herein, refers to compounds wherein the basic nitrogen atom of either a heteroaromatic ring or tertiary amine is oxidized to give a quaternary nitrogen bearing a positive formal charge and an attached oxygen atom bearing a negative formal charge.

The term "pharmaceutically acceptable salt", as used herein, refers to the acid addition salts derived from organic and inorganic acids. Such salts include but are not limited to, the acetate, adipate, alginate, aspartate, benzoate, benzenesulfonate, bisulfate, butyrate, citrate, camphorate, camphorsulfonate, cinnamoate, dodecylsulfate, ethanesulfonate, fumarate, glycerophosphate, glycolate, hemisulfate, hydrochloride, hydrobromide, hydroiodide, lactate, maleate, malonate, mandelate, methanesulfonate, nicotinate, nitrate, oxalate, pamoate, pectinate, phosphate, pivalate, propionate, pyruvate, salicylate, succinate, tartrate, toluenesulfonate and tosylate. Also included are the salts formed when a basic nitrogen-containing group is quaternized with such agents as a lower alkyl halide, dialkyl sulfate, long chain halide such as lauryl bromide, aralkyl halides such as benzyl and phenethyl bromide.

"Effective amount" refers to an amount of a compound as described herein that may be effective to inhibit, prevent, or treat the symptoms of particular disease or disorder. Such diseases and disorders include, but are not limited to, those pathological conditions associated with the administration of $5\text{-HT}_{1A}$ antagonists (for example, in connection with the treatment and/or prevention of depression), wherein the treatment or prevention comprises, for example, inhibiting the activity thereof by contacting cells, tissues or receptors with compounds of the present invention. Thus, for example, the term "effective amount", when used in connection with $5\text{-HT}_{1A}$ antagonists, for example, for the treatment of depression, refers to the treatment and/or prevention and/or amelioration of the condition.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

"In combination with," refers, in certain embodiments, to the concurrent administration to a patient of SSRI's and the compounds of formula (I). When administered in combination, each component may be administered at the same time or sequentially in any order at different points in time. Thus, each component may be administered separately but sufficiently closely in time so as to provide the desired therapeutic effect.

"Dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

"Patient" refers to animals, including mammals, preferably humans.

The terms "administer", "administering" or "administration", as used herein, refer to either directly administering a compound or composition to a patient, or administering a prodrug derivative or analog of the compound to the patient, which will form an equivalent amount of the active compound or substance within the patient's body.

The present invention accordingly provides pharmaceutical compositions that include the compound of formula (I); and optionally one or more pharmaceutically-acceptable carriers, excipients, or diluents. The term "carrier", as used herein, shall encompass carriers, excipients and diluents. Examples of such carriers are well known to those skilled in the art and are prepared in accordance with acceptable pharmaceutical procedures, such as, for example, those described in *Remington's Pharmaceutical Sciences,* 17th edition, ed. Alfonso R. Gennaro, Mack Publishing Company, Easton, Pa. (1985), which is incorporated herein by reference in its entirety. Pharmaceutical acceptable carriers are those carriers that are compatible with the other ingredients in the formulation and are biologically acceptable.

The compounds of formula (I) can be administered orally or parenterally, neat, or in combination with conventional pharmaceutical carriers.

Representative solid carriers include one or more substance that can act as flavoring agents, lubricants, solubilizers, suspending agents, fillers, glidants, compression aids, binders, tablet-disintegrating agents, or encapsulating materials. They are formulated in conventional manner, for example, in a manner similar to that use for known antihypertensive agents, diuretics and β-blocking agents. Oral formulations containing the active compounds of this invention may comprise any conventionally used oral forms, including tablets, capsules, buccal forms, troches, lozenges and oral liquids, suspensions or solutions. In powders, the carrier is a finely divided solid that is in admixture with the finely divided active ingredient. In tablets, the active ingredient is mixed with a carrier having the necessary compression properties in suitable proportion and compacted in the shape and size desired. The powders and tablets preferably contain up to 99% of the active ingredient.

Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, microcrystalline cellulose, methyl cellulose, sodium carboxymethyl cellulose, carboxymethylcellulose calcium, polyvinylpyrrolidine, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, starches, sugars, low melting waxes, and ion exchange resins. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed.

Liquid carriers can be used in preparing solutions, suspensions, emulsions, syrups, and elixirs. The active ingredient can be dissolved or suspended in a pharmaceutically acceptable oil or fat. The liquid carrier can obtain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions that are sterile solutions or suspensions can be administered by, for example, intramuscular, intraperitoneal, or subcutaneous injection. Sterile solutions can also be administered intravenously. Compositions for oral administration may be in either liquid or solid form.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

When administered for the treatment, prevention or amelioration of a particular disease state or disorder, it is understood that the effective dosage may vary depending upon the particular compound utilized, the mode of administration, the condition, and severity thereof, of the condition being treated, as well as the various physical factors related to the individual being treated. In therapeutic applications, compounds of formula (I) are provided to a patient already suffering from a disease in an amount sufficient to cure or at least partially ameliorate the symptoms of the disease and its complications. An amount adequate to accomplish this is defined as an "effective amount." The dosage to be used in the treatment of a specific case must be subjectively determined by the attending physician. The variables involved include the specific condition and the weight, age, and response pattern of the patient. Effective administration of the compounds of this invention may be given at an oral dose of from about 0.1 mg/day to about 1,000 mg/day. Preferably, administration will be from about 10 mg/day to about 600 mg/day, more preferably from about 50 mg/day to about 600 mg/day, in a single dose or in two or more divided doses. The projected daily dosages are expected to vary with route of administration.

Such doses may be administered in any manner useful in directing the active compounds herein to the patient's bloodstream, including orally, via implants, parentally (including intravenous, intraperitoneal, intraarticularly and subcutaneous injections), rectally, intranasally, topically, ocularly (via eye drops), vaginally, and transdermally.

In some cases it may be desirable to administer the compounds directly to the airways in the form of an aerosol. For administration by intranasal or intrabronchial inhalation, the compounds of formula (I) can be formulated into an aqueous or partially aqueous solution.

The compounds of this invention may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The compounds of formula (I) can also be administered transdermally through the use of a transdermal patch. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

The compounds of formula (I) may be administered rectally or vaginally in the form of a conventional suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

Since prodrugs are known to enhance numerous desirable qualities of pharmaceuticals (e.g., solubility, bioavailability, manufacturing, etc.) the compounds employed in the present methods may, if desired, be delivered in prodrug form. Thus, the present invention contemplates methods of delivering prodrugs. Prodrugs of the compounds employed in the present invention, for example formula (I), may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

Various forms of prodrugs are known in the art such as those discussed in, for example, Bundgaard (ed.), *Design of Prodrugs*, Elsevier (1985); Widder, et al. (ed.), *Methods in Enzymology*, Volume 4, Academic Press (1985); Krogsgaard-Larsen, et al., (ed.), *Design and Application of Prodrugs, Textbook of Drug Design and Development*, Chapter 5, 113–191 (1991); Bundgaard, et al., *Journal of Drug Delivery Reviews* 1992, 8, 1–38; Bundgaard, *Journal of Pharmaceutical Sciences* 1988, 77, 285 et seq.; Higuchi and Stella (eds.), *Prodrugs as Novel Drug Delivery Systems*, American Chemical Society (1975), each of which is incorporated by reference in its entirety.

The compounds employed in the methods of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl group. Other preferred protecting groups that may be employed in accordance with the present invention may be described in Greene, T. W. and Wuts, P. G. M., *Protective Groups in Organic Synthesis* 2d. Ed., Wiley & Sons, 1991.

This invention also provides methods of utilizing the compounds of this invention, or a pharmaceutically acceptable salt thereof, in preventing, treating or ameliorating anxiety, generalized anxiety disorder, depression, schizophrenia, cognitive deficits resulting from neurodegenerative diseases like Alzheimer's Disease, and in the treatment of prostate cancer. The compounds of this invention can also be used in the treatment, enhancement, or facilitation of smoking cessation or in comparable methods of assisting in withdrawal of nicotine-related habits. Each of these methods comprises administering to a mammal in need thereof, preferably a human in need thereof, of a pharmaceutically effective amount of a compound of this invention, or a pharmaceutically acceptable salt thereof.

This invention also provides for the use of the compounds of the invention for the manufacture of a medicament for treating a central nervous system (CNS) disorder, for treating prostate cancer or for treating withdrawal symptoms induced by cessation of smoking or use of nicotine-containing products.

This invention also provides methods for enhancing the efficacy of selective serotonin reuptake inhibitors (SSRIs) in a mammal, the methods comprising co-administering to a mammal in need thereof pharmaceutically effective amounts of the SSRI in question and a compound of formula (I). Among the SSRIs that may be administered in these regimens are fluoxetine hydrochloride, venlafaxine hydrochloride, paroxetine hydrochloride, nefazodone hydrochloride, and sertraline hydrochloride. It will be understood that the SSRIs in these regimens may be administered in dosages and regimens known in the art for these compounds. These methods may also be characterized as methods of treatment of maladies such as depression, anxiety and generalized anxiety disorder in a mammal in need thereof, the methods comprising co-administering to the mammal in need thereof of pharmaceutically effective amounts of a compound of this invention, or a pharmaceutically acceptable salt thereof, and an SSRI.

Anxiety

While no clinical trial results have been published, 5-$HT_{1A}$ antagonists have demonstrated anxiolytic activity in several animal models, most notably the elevated plus-maze (D. J. Bill and A. Fletcher, *Br. J. Pharmacol.* 1994, 111, 151P; J-L. Moreau, et al., *Brain Res. Bull.* 1992, 29, 901) and the light/dark box (R. J. Rodgers and J. C. Cole, *Eur. J. Pharmacol.* 1994, 261, 321). Therefore, 5-$HT_{1A}$ antagonists may find use as anxiolytic agents.

Depression

The 5-$HT_{1A}$ receptor appears to play a major role in mediating antidepressant response (J. F. Deakin, et al., *Trends Pharmacol. Sci.*, 1993, 14, 263). The delay in onset of antidepressant activity seen with serotonin-specific release inhibitors (SSRI's) is a result of the activation of somatodendritic 5-$HT_{1A}$ autoreceptors and a resulting decrease in serotonin release (S. Hjorth and S. B. Auerbach, *Behav. Brain Res.* 1996, 73, 281). Several clinical studies that combined the 5-$HT_{1A}$ antagonist pindolol with several selective serotonin reuptake inhibitors (SSRI's, e.g., paroxetine) indicate that addition of the 5-$HT_{1A}$ antagonist hastens the onset of action of the SSRI and may even enhance the potency of the SSRI (Schechter et al., *Current Opinion in CPNS Investigational Drugs* 1999, 1, 432). Chronic administration of the SSRI leads to an eventual desensitization of the 5-$HT_{1A}$ autoreceptor, an increase in neuronal firing and serotonin release and concomitant antidepressant activity.

Schizophrenia

Evidence has accumulated over the last decade to suggest that serotonin and various serotonin receptors play a role in the pathophysiology and pharmacological treatment of schizophrenia. Both receptor binding studies (T. Hashimoto, et al., *Life Sci.*, 1991, 48, 355) and autoradiography (J. N. Joyce, et al., *Neuropsychopharmacol.* 1993, 8, 315; P. W. J. Bumet, et al., *Neuropsychopharmacol.*, 1996, 15, 442) on postmortem brains of schizophrenia patients indicate that there is an increase in 5-$HT_{1A}$ receptor density. While the most efficacious antipsychotic treatments to date have targeted dopaminergic neurotransmission, it is clear from binding results that atypical antipsychotics also possess significant serotonergic affinity (H. Y. Meltzer, *Clin. Neurosci.* 1995, 3, 64). Notably, the 5-$HT_{1A}$ receptor has been associated with changes in dopaminergic neurotransmission (M. Hamon, et al., *J. Pharmacol. Exp. Ther.* 1988, 246, 745; L. E. Schechter, et al., *J. Pharmacol. Exp. Ther.* 1990, 255, 1335). Furthermore, dysfunctional glutamatergic pathways appear to be involved in psychotic pathology and decreased glutamate levels have been demonstrated in schizophrenic brains (K. Q. Do, et al., *J. Neurochem.* 1995, 65, 2652; G. C. Tsai, et al., *Arch. Gen. Psychiatry* 1995, 52, 829). Thus, by enhancing glutamate availability and transmission, 5-$HT_{1A}$ antagonists may function as antipsychotic agents.

Cognitive Deficits from Neurodegenerative Disorders

Alzheimer's disease is characterized by a loss in both cholinergic and glutamatergic excitatory neurotransmission.

Numerous preclinical studies suggest that blockade of 5-HT$_{1A}$ receptors may compensate for the loss in glutamatergic excitatory input seen in Alzheimer's Disease by enhancing glutamate release (see Schechter et al., *Current Pharmaceutical Design* 2002, 8, 139), and references cited therein). Furthermore, 5-HT$_{1A}$ antagonists may compensate for Alzheimer-related cholinergic deficits by enhancing glutamatergic transduction through the same pathway. Recently, it has been demonstrated that 5-HT$_{1A}$ antagonists can reverse cholinergic- and glutamatergic-associated cognitive deficits in animal models, including fomix lesion (Harder et al., *Psychopharmacol.* 1996, 127, 245), scopolamine-induced deficits (Carli et al, *Eur. J. Pharmacol.* 1995, 283, 133) and MK-801-induced deficits (Harder et al., *Neuropharmacology,* 2002, 39, 547). Thus, 5-HT$_{1A}$ antagonists may provide relief of the cognitive deficits seen in Alzheimer's disease.

Studies on the cholinergic deficits observed in Alzheimer's disease have made it apparent that not all patients can be characterized by deficits in this system alone (P. T. Francis, et al., *Neurotransmitters and Neuropeptides in Alzheimer's Disease,* R. D. Terry, ed., Raven Press, Ltd., New York, 247–261 (1994)). More recent studies reveal that glutamatergic function is also severely disrupted. Glutamate is an important neurotransmitter that can enhance cognition and physiological phenomena such as long-term potentiation (LTP), which appears to play a role in mediating learning and memory processes. The activation of glutamatergic neurotransmission facilitates memory (U. Stabil, et al., *PNAS* (USA) 1994, 91, 777), while glutamate antagonists impair learning and memory as well as LTP in rats (R. G. Morris, et al., *Nature* 1986, 319, 774; T. V. Bliss and G. L. Collinridge, *Nature* 1993, 361,31).

Studies on the post-mortem brains of Alzheimer's patients have demonstrated reductions in glutamate receptors in both neocortex and hippocampus (J. T. Greenmyre, *Arch. Neurol.* 1986, 43, 1058; W. F. Marangos, et al., *Trends Neurosci.* 1987, 10, 37). Rich in glutamatergic neurons, the pyramidal cell layer of the entorhinal cortex is one of the first areas in the Alzheimer's brain to develop the morphological hallmarks of Alzheimer's disease, plaques and tangles. Furthermore, there are reduced levels of glutamate in the perforant pathway that projects from the entorhinal cortex to the dentate gyrus (B. T. Hyman, et al., *Ann. Neurol.* 1987, 22, 37) and a loss of glutamate staining in the perforant path terminal zone that has been associated with Alzheimer's Disease (N. W. Kowal and M. F. Beal, *Ann. Neurol.* 1991, 29, 162). Thus, there is compelling evidence that a deficit in glutamatergic neurotransmission is associated with cognitive impairment and is a pathological finding in Alzheimer's Disease.

Data indicate that 5-HT$_{1A}$ antagonists have a facilitatory effect on glutamatergic neurotransmission (D. M. Bowen, et al., *Trends Neurosci.* 1994, 17, 149). Serotonin 5-HT$_{1A}$ antagonists have been shown to both potentiate NMDA-induced glutamate release from pyramidal neurons and significantly elevate glutamate release when administered alone (S. N. Dilk, et al., *Br. J. Pharmacol.* 1995, 115, 1169). They inhibit the tonic hyperpolarizing effect of serotonin on neurons in both the cortex and hippocampus, which in turn enhances glutamatergic neurotransmission and signaling (R. Araneda and R. Andrade, *Neuroscience* 1991, 40, 399). Coupled with the observation that a functionally hyperresponsive serotonin system in Alzheimer's disease may contribute to the cognitive disturbances (D. M. McLoughlin, et al., *Am. J. Psychiatry* 1994, 151, 1701), the data suggest that 5-HT$_{1A}$ antagonists may improve cognition by removing the inhibitory effects of endogenous serotonin on pyramidal neurons and enhancing glutamatergic activation and the ensuing signal transduction.

Nevertheless, the cholinergic system clearly plays a role in cognitive processing, and recent therapies designed to improve cognition in Alzheimer's patients have been targeted at enhancing cholinergic neurotransmission, either through inhibition of acetylcholinesterase or by the use of agonists. Postsynaptic M1muscarinic acetylcholine receptors are located on pyramidal neurons along with glutamatergic and 5-HT$_{1A}$ receptor sites. In this regard, blockade of 5-HT$_{1A}$ receptors may compensate for the loss of cholinergic excitatory input by enhancing glutamatergic transduction through the same pathway. In fact, muscarinic (M1) signal transduction may be facilitated by blocking the hyperpolarizing action of serotonin. In addition, there is evidence that 5-HT$_{1A}$ receptor antagonists may decrease the formation of β-amyloid plaques and tangles via its enhancement of muscarinic M1 receptor signaling and resulting activation of protein kinase C (J. D. Baxbaum, et al., *PNAS* (USA), 1993, 90, 9195).

Preclinical evidence for treating Alzheimer's disease has been established using available 5-HT$_{1A}$ antagonists. WAY-100635 reversed the cognitive deficits induced by fomix lesions in marmosets (J. A. Harder, et al, *Psychopharmacol.* 1996, 245). WAY-100135 prevented the impairment of spatial learning caused by intrahippocampal scopolamine, a muscarinic antagonist (M. Carli, et al., *Eur. J. Pharmacol.* 1995, 283, 133). NAN-190 has been shown to augment LTP (N. Sakai and C. Tanaka, *Brain Res.* 1993, 613, 326). Taken together with the various in vitro data described above and in the literature, these studies strongly suggest that treatment with 5-HT$_{1A}$ receptor antagonists represent a viable strategy for restoring the multiple deficits associated with Alzheimer's disease.

Enhancement of Antidepressant Activity

Co-administration of a 5-HT$_{1A}$ antagonist would be expected to inhibit the SSRI-induced activation of presynaptic autoreceptors and, thus, hasten the onset of antidepressant action of SSRI's. This hypothesis is supported by results from studies in animal models using more- or less-specific 5-HT$_{1A}$ antagonists in combination with SSRI's (K. Briner and R. C. Dodel, *Cur. Pharm. Des.* 1998, 4, 291), and references cited therein). Furthermore, clinical trials have shown that co-administration of the 5-HT$_{1A}$ antagonist pindolol significantly reduced the median time needed to achieve a sustained antidepressant response with the SSRI's paroxetine (M. B. Tome, et al., *Int. Clin. Psy.* 1997, 12, 630) and fluoxetine (V. Perez, et al., *Lancet* 1997, 349, 1594). Therefore, 5-HT$_{1A}$ antagonists are expected to enhance the antidepressant activity of SSRI's by reducing the delay in onset of action seen with this class of drugs.

Prostate Cancer

In addition to its role as a neurotransmitter, serotonin can function as a growth factor. Serotonin is found in most neuroendocrine cells of the human prostate, where it may play a role in the progression of prostate carcinoma (P. A. Abrahamsson, et al., *Pathol. Res. Pract.* 1986, 181, 675; N. M. Hoosein, et al., *J. Urol.* 1993, 149, 479A). The 5-HT$_{1A}$ antagonist pindobind has shown antineoplastic activity when tested against the human prostate tumor cell lines PC3, DU-145 and LNCaP in vitro and inhibited the growth of the aggressive PC3 cell line in vivo in athymic nude mice (M. Abdul, et al., *Anticancer Res.* 1994, 14, 1215).

Smoking Cessation

Cessation from chronic use of nicotine or tobacco in humans results in withdrawal symptoms, including anxiety, irritability, difficulty concentrating and restlessness. These withdrawal symptoms have been shown to play an important role in relapse (J. R. Hughes and D. Hatsukami, *Arch. Gen. Psychiatry* 1986, 43, 289). Preclinical evidence indicates that withdrawal from the chronic administration of nicotine increases the sensitivity of $5\text{-HT}_{1A}$ receptors (K. Rasmussen and J. F. Czachura, *Psychopharmacology* 1997, 133, 343) and enhances the auditory startle reflex in rats (D. R. Helton, et al., *Psychopharmacology* 1993, 113, 205). Serotonin $5\text{-HT}_{1A}$ antagonists have been shown to attenuate this nicotine-withdrawal-enhanced startle response (K. Rasmussen, et al., *Synapse* 1997, 27, 145; K. Rasmussen, et al., *J. Pharmacol. Exp. Ther.* 2000, 294, 688). Thus, $5\text{-HT}_{1A}$ antagonists may find clinical use as a pharmacotherapy for smoking cessation. This excess serotonin activates somatodendritic autoreceptors, $5\text{-HT}_{1A}$ receptors, which reduces cell firing activity and, in turn, causes a decrease in serotonin release in major forebrain areas. This negative feedback limits the increment of synaptic serotonin that can be induced by antidepressants acutely.

Recent studies also provide evidence that the anxiogenic effects induced by withdrawal of nicotine are partially or primarily mediated by $5\text{-HT}_{1A}$ receptors in various parts of the brain, including dorsal hippocampus (Kenny et al., *Neuropharmacology* 2000, 39, 300), dorsal raphe nucleus (Cheeta, *Psychopharmacology* 2001, 155, 78) and lateral septum (File et al., *Eur. J. Pharmacol.* 2000, 393, 231). In animal models, anxiogenic behaviors induced by nicotine withdrawal can be blocked by treatment with $5\text{-HT}_{1A}$ antagonists, including NAN-190, LY206130, WAY-100635 (Rasmussen et al., *Synapse* 1997, 27, 45) and LY 426965 (Rasmussen et al., *J. Pharmacol. Exp. Ther.* 2000, 294, 88). Thus, $5\text{-HT}_{1A}$ antagonists may find use in the treatment of the withdrawal symptoms induced by cessation of smoking and the use of other nicotine-containing products.

This invention also provides pharmaceutical compositions utilizing the compounds of this invention. Each composition comprises an effective amount of a compound of this invention and one or more pharmaceutically acceptable carriers or excipients.

The variables involved in determining a desirable dose for an individual recipient include the specific disease or disorder and the size, age and response pattern of the patient. The novel method of the invention for treating conditions related to or are affected by the $5\text{-HT}_{1A}$ receptor comprise administering to warm-blooded animals, including humans, an effective amount of at least one compound of this invention or its pharmaceutically acceptable salt form. The compounds may be administered orally, rectally, parenterally or topically to the skin and mucosa. A daily human dose may be administered from about 0.01–1000 mg/kg for oral application, preferably 0.5–500 mg/kg, and 0.1–100 mg/kg for parenteral application, preferably 0.5–50 mg/kg.

Applicable solid carriers can include one or more substances which may also act as flavoring agents, lubricants, solubilizers, suspending agents, fillers, glidants, compression aids, binders or tablet-disintegrating agents or encapsulating materials. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient in this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferable sodium carboxymethyl cellulose solution), alcohols (including monohydric alcohols and polyhydric alcohols, e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

The compounds of formula (I) can be prepared by known methods from known starting materials that are available by conventional methods. Such methods include acylating an amine of formula (II) (where $R_1$ is as defined above) with bicyclic carboxylic acids of general formula (III) (where $R_2$ is defined above) or an acylating derivative thereof. Examples of acylating derivatives include the acid halides (e.g., acid chloride), anhydrides, imidazolides (e.g., obtained form carbonyldiimidazole) and activated esters.

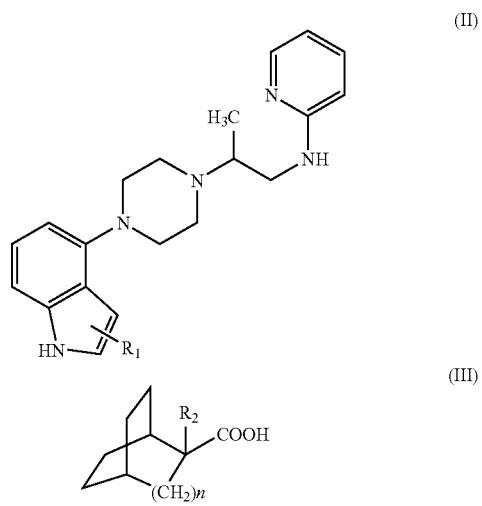

The starting materials of formula (II) may be prepared by the general route disclosed in EP-B1-0,512,755 and specifically by the exemplified route described in WO 95/33743, the disclosures of which are incorporated herein by reference.

Reaction of cyclohexadiene with an acrylate ester derivative using literature methods (Tichy et al., *Coll. Czech. Chem. Commun.* 1970, 35, 459; Boehme et al., *J. Am. Chem. Soc.* 1958, 80, 5488) provides bicyclo[2.2.2]cyclooct-5-ene ester derivatives of formula (IV), which may be reduced (using, for example, 10% palladium on carbon under a hydrogen atmosphere as in Christol et al., *Org. Magn. Res.* 1981, 17, 110) to give saturated bicyclic esters of formula (V). Hydrolysis (for example, using a base such as sodium hydroxide in a suitable solvent such as methanol) provides the required racemic starting material of formula (III) (Scheme 1).

Scheme 1

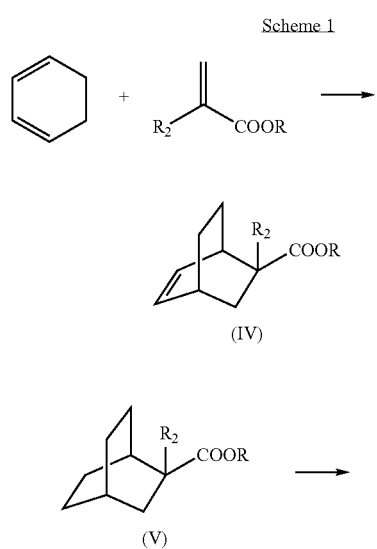

(IV)

(V)                    (III)

The individual enantiomers of bicyclo[2.2.2]octane-2-carboxylic acids may be obtained through separation of the racemic mixture by methods known to one skilled in the art of organic synthesis. Alternatively, the enantiomers of bicyclo[2.2.2]octane-2-carboxylic acid may be obtained via a synthetic route that utilizes a chiral auxiliary reagent in an intermolecular Diels-Alder reaction. Such conditions are known and have been used to prepare bicyclo[2.2.2]oct-5-ene ester derivatives. For example, compound of formula (VIa) was synthesized according to Hansen et al. (*J. Org. Chem.* 1998, 63, 775), and, after hydrogenation of the double bond (using, for example, 10% palladium on carbon in an alcoholic solvent), the chiral auxiliary ester moiety could be removed under the influence of a base such as lithium hydroxide to provide the (S)-enantiomer of bicyclo[2.2.2]octane-2-carboxylic acid of formula(IIIa), as shown in Scheme 2.

Scheme 2

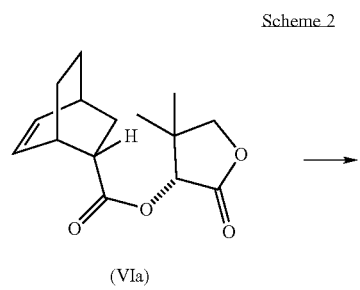

(VIa)

-continued

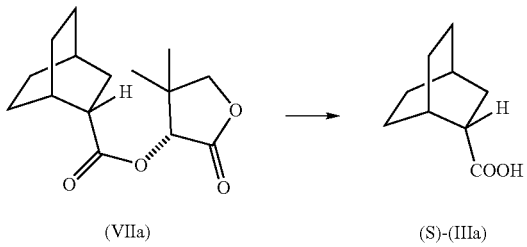

(VIIa)                    (S)-(IIIa)

The opposite (R)-enantiomer of bicyclo[2.2.2]octane-2-carboxylic acid can be prepared as shown in Scheme 3, by utilizing the opposite enantiomer of the chiral auxiliary reagent, and the methodology reported by Hansen et al. (*J. Org. Chem.* 1998, 63, 775). Thus treatment of the ester (VIb), using the conditions shown in Scheme 2, provided the ester (VIIb), which provided, upon hydrolysis, the (R)-enantiomer of bicyclo[2.2.2]octane-2-carboxylic acid (IIIb).

Scheme 3

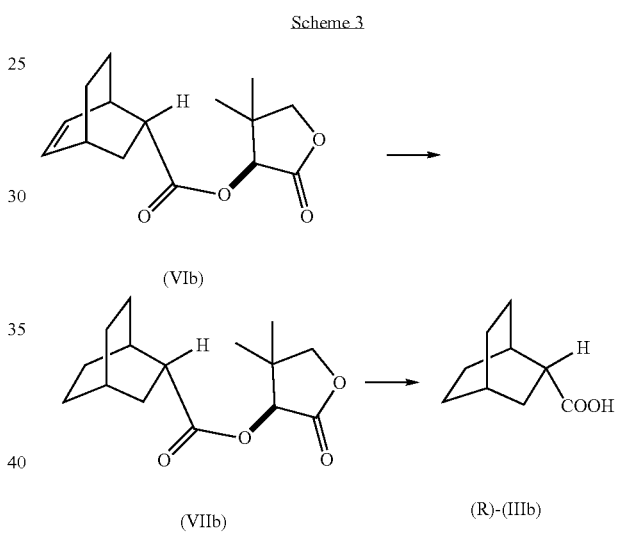

(VIb)

(VIIb)                    (R)-(IIIb)

The required bicyclo[2.2.1]heptane-7-carboxylic acid of formula (VM) can be prepared as shown in Scheme 4, using the procedure described by Stapersma and Klump (*Tetrahedron* 1981, 37, 187), wherein 7-bromobicyclo[2.2.1]heptane is treated with lithium di-t-butylbiphenylide (Freeman and Hutchinson, *Tet. Lett.* 1976, 1849), followed by carbon dioxide.

Scheme 4

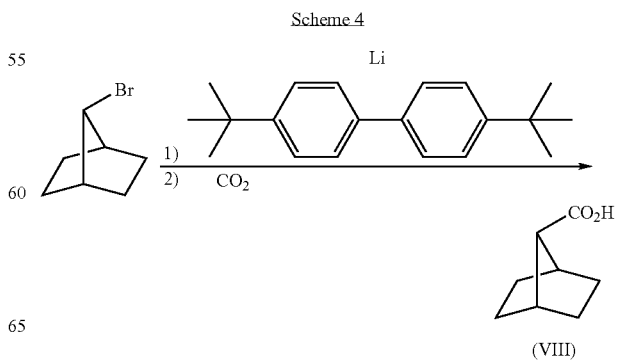

(VIII)

The 7-substituted bicyclo[2.2.1]heptane-7-carboxylic acid intermediates of formula (XII) can be prepared according to literature procedures, for example, as outlined in Scheme 5. A Diels-Alder reaction between cyclopentadiene and an appropriate acrylic acid affords exo-2-alkyl bicyclo [2.2.1]heptene-2-carboxylic acids of formula (IX). An acid-catalyzed rearrangement provides lactones of formula (X), which can be hydrolyzed in situ and oxidized to the desired 7-substituted bicyclo[2.2.1]heptan-2-one-7-carboxylic acids of formula (XI) with ruthenium tetroxide (generated in situ from ruthenium chloride and sodium periodate). A Wolff-Kishner reduction yields the final product (XII).

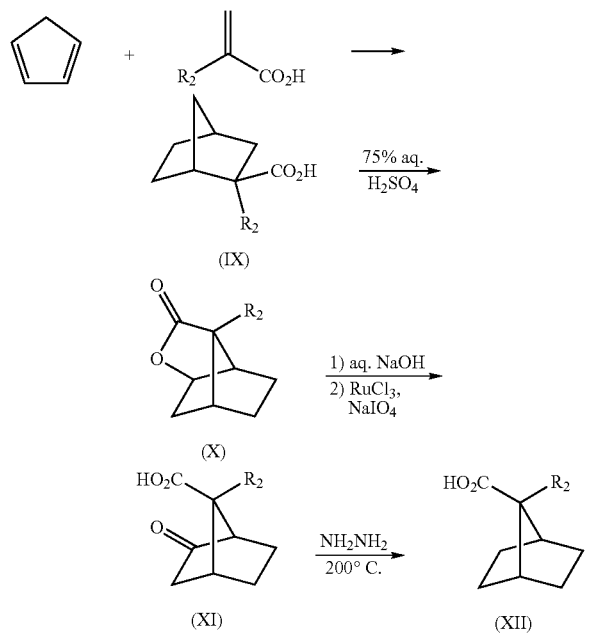

Scheme 5

The present invention will now be illustrated by reference to the following specific, non-limiting examples. Those skilled in the art of organic synthesis may be aware of still other synthetic routes to the invention compounds. The reagents and intermediates used herein are either commercially available or prepared according to standard literature procedures.

EXAMPLES

Intermediate 1: Bicyclo[2.2.2]octane-2-Carboxylic Acid

Sodium hydroxide (2.5N, 22.4 mL, 56 mmol) was added to a methanolic solution of methyl bicyclo[2.2.2]octane-2-carboxylate (4.7 g, 28 mmol in 50 mL) at ambient temperature and the mixture was stirred for 16 hours. The solvent was concentrated in vacuo, water added (20 mL) and the solution made acidic with IN aqueous HCl. The product was extracted into dichloromethane (3×50 mL), the combined organic layers washed with water (25 mL), dried over anhydrous magnesium sulfate, filtered and concentrated on a rotary evaporator to afford the titled compound of formula (III) as a white solid (4.3 g, 100% yield).
MS (ESI) m/z=: 155 (M+H)$^+$.
Elemental Analysis for: $C_9H_{14}O_2$
Calculated: C, 70.10; H, 9.15.
Found: C, 70.53; H, 9.25.

Intermediate 2: (3R)-4,4-Dimethyl-2-oxotetrahydro-furan-3-yl-(2S)-bicyclo[2.2.2]oct-5-ene-2-carboxylate Compound (VIa) was synthesized according to Hansen et al. (*J. Org. Chem.* 1998, 63, 775) in two steps starting from (R)-(−)-pantolactone (11.5 g, 88.4 mmol) and acroloyl chloride (10.14 g, 112 mmol). It was obtained as a light yellow powder by recrystallization from diethyl ether/hexane.
MS (+ESI) m/z=265 (M+H)$^+$.
Elemental Analysis for: $C_{15}H_{20}O_4$
Calculated: C, 68.16; H, 7.63.
Found: C, 67.87; H, 7.68.

Intermediate 3: (3R)4,4-Dimethyl-2-oxotetrahydro-furan-3-yl-(2S)-bicyclo[2.2.2]octane-2-carboxylate To the solution of compound (VIa) (Intermediate 2, 20 g, 75.8 mmol) in methanol (100 mL) was added a catalytic amount of 10% palladium on carbon (1 g) and the mixture was hydrogenated in a Parr shaker at 40 psi. After three hours, the mixture was filtered through a bed of celite, the catalyst was washed with methanol and the solution concentrated and dried under vacuum. The crude product of formula (VIIa) was obtained as a light brown solid which was used without any further purification (18.2 g, 90%).
MS (+ESI) m/z=267 (M+H)$^+$.
Elemental Analysis for: $C_{15}H_{22}O_4$
Calculated: C, 67.64; H, 8.33.
Found: C, 67.00; H, 8.52.

Intermediate 4: (S)-Bicyclo[2.2.2]octane-2-carboxylic Acid

The product of formula (VIIa) (Intermediate 3, 18.0 g, 67.7 mmol) was dissolved in tetrahydrofuran (100 mL) and the resulting solution cooled to 5–10° C. A solution of lithium hydroxide (7 g) in water (140 mL) was added slowly, maintaining the reaction temperature to below 25° C. and the mixture was stirred for 24 hours at room temperature, then concentrated in vacuo until most of tetrahydrofuran had been removed. Concentrated HCl was added drop-wise to adjust the pH to 2, water (60 mL) was added and the slurry stirred at 0–10° C. for one hour. The precipitate was isolated by filtration, and dried in a vacuum oven. The crude product of formula (IIIa) was used without any further purification (9.35 g, 90%).
MS (−ESI) m/z=153 (M−H)$^-$.
Elemental Analysis for: $C_9H_{14}O_2$
Calculated: C, 70. 10; H, 9.15.
Found: C, 69.50; H, 9.22.

Intermediate 5: (R)-Bicyclo[2.2.2]octane-2-carboxylic Acid

The (R)-enantiomer of formula (IIIb) was prepared, starting from (S)-(+)-pantolactone (10 g, 76.9 mmol) and acryloyl chloride (8.81 g, 97.4 mmol), using the method of Hansen *et. al., J Org. Chem.* 1998, 63, 775) and the synthetic methods described for Intermediates 3 and 4.
MS (−ESI) m/z=153 (M−H)$^{31}$ .
Elemental Analysis for: $C_9H_{14}O_2$
Calculated: C, 70.10; H, 9.15.
Found: C, 69.97; H, 9.10.

Intermediate 6: Bicyclo[2.2.1]heptane-7-carboxylic Acid

To a solution of 4-4'-di-t-butylbiphenyl (8.25 g, 31 mmol) in anhydrous tetrahydrofuran (70 mL) under a nitrogen atmosphere was added freshly cleaned lithium wire (0.21 g, 30 mmol). The resulting mixture was stirred at room temperature for 15 minutes to initiate reaction, then cooled in an ice bath and stirred for an additional 4 hours. The resulting blue solution was cooled with a dry ice/acetone bath and a solution of 7-bromo-bicyclo[2.2.1]heptane (2.0 g, 11.4 mmol) in anhydrous tetrahydrofuran (5 mL) was added in one portion. The reaction mixture was stirred for 20 minutes, during which time the blue color changed to orange. Solid dry ice was then added to the reaction, which became colorless. The dry ice bath/acetone bath was removed and the reaction was stirred for 2 hours, during which time it came up to room temperature. 2.5 N aqueous sodium hydroxide (200 mL) was added and the mixture was stirred for 5 minutes. The layers were separated and the aqueous layer was extracted twice with diethyl ether (50 mL). The aqueous layer was then made acidic by addition of concentrated HCl and extracted with three portions of diethyl ether (75 mL). The combined organic layers were dried over anhydrous magnesium sulfate and concentrated to yield the desired compound of formula (VIII) as a white solid (1.54 g, 96%), mp=74–75 ° C. (lit. mp=77.5–785° C., $J. Am. Chem. Soc.$ 1954, 76, 4072).

MS 9–ESI) m/z=139 $(M-H)^-$.
Elemental Analysis for $C_8H_{12}O_2$
Calculated: C, 68.55; H, 8.63.
Found: C, 67.97; H, 8.57.

Intermediate 7: Exo-2-methylbicyclo[2.2.1]hept-5-ene-2-carboxylic Acid

A mixture of cyclopentadiene (freshly prepared from dicyclopentadiene, 62.0 g, 0.94 mol) and methacrylic acid (69.8 g, 0.81 mol) was refluxed at 90° C. for four hours. The resulting mixture was subjected to vacuum distillation under reduced pressure (2 mm). The fraction boiling between 69° C. and 110° C. was collected and yielded a white solid upon standing, which was shown to be a mixture of the endo-and exo-isomers, with the exo-isomer predominating. The pure exo-2-methyl-bicyclo[2.2.1]heptene-2-carboxylic acid of formula (IX) was isolated from the mixture by recrystallizing twice from petroleum ether (bp 40–60° C.), to give 30.5 g of the desired product as a white solid, mp=82–83° C. (lit. mp=82-83 ° C., $J. Org. Chem.$ 1979, 44, 2206).

MS (–ESI) m/z=151 $(M-H)^-$.
Elemental Analysis for $C_9H_{12}O_2$
Calculated: C, 71.03; H, 7.95.
Found: C, 71.37; H, 8.19.

Intermediate 8: 3a-Methylhexahydro-3H-1,4-methanocyclopenta[c]furan-3-one

Exo-2-methyl-bicyclo[2.2.1]heptene-2-carboxylic acid (8.06 g, 53 mmol, Intermediate 7) was treated under ice cooling with 75% aqueous sulfuric acid (100 mL). The resulting mixture was stirred overnight, during which time it came up to room temperature. The reaction was then poored onto a mixture of ice and water (1000 g) and a white precipitate forms. The resulting mixture was extracted with three 200 mL portions of diethyl ether. The combined organic layers were dried over anhydrous magnesium sulfate and concentrated on a rotary evaporator to yield a white solid (7.73 g). The solid was recrystallized from ethanol to give the desired product of formula (X) as white needles (5.9 g, 73%), mp=125–127 ° C. (lit. mp=125–126 ° C., $J. Org. Chem.$ 1979, 44, 2206).

MS (+ESI) m/z=153 $(M+H)^+$.
Elemental Analysis for $C_9H_{12}O_2$
Calculated: C, 71.03; H, 7.95.
Found: C, 70.92; H, 8.10.

Intermediate 9: 7-Methyl-2-oxobicyclo[2.2.1]heptane-2-carboxylic Acid

The product from Intermediate 8 (compound of formula (X), 4.9 g, 32.2 mmol) was suspended in 0.5 N aqueous sodium hydroxide (70 mL, 35 mmol) and stirred at 100° C. for 45 minutes, during which time a clear solution formed. The resulting solution was cooled to room temperature and two drops of 1% ethanolic phenolphthalein solution were added. The solution was then neutralized with 0.1 N aqueous HCl. To the neutral solution was added water (35 mL), carbon tetrachloride (33 mL) and acetonitrile (33 mL). To the stirred reaction mixture was then added ruthenium (III) chloride hydrate (0.25 g), followed by sodium periodate (20.67 g, 96.6 mmol). The resulting mixture was then stirred at room temperature for 24 hours, then water (50 mL) and diethyl ether (100 mL) were added. Stirring was continued for 5 minutes, then the layers were separated. The aqueous layer was extracted twice more with diethyl ether (50 mL). The combined organic layers were dried over anhydrous magnesium sulfate and concentrated on a rotary evaporator to yield a purple solid. The solid was dissolved in diethyl ether (75 mL) and filtered through a bed of celite to remove the remaining purple impurity. The clear solution was concentrated on a rotary evaporator to yield the desired product of formula (XI) as a white solid (3.16 g, 58%), mp=204–206 ° C. (lit. mp=206–208 ° C., $Tetrahedron$ 1972, 28, 4259).

MS (–ESI) m/z=167 $(M-H)^-$.
Elemental Analysis for $C_9H_{12}O_3$
Calculated: C, 64.27; H, 7.19.
Found: C, 63.74; H, 7.31.

Intermediate 10: 7-Methylbicyclo[2.2.1]heptane-7-carboxylic Acid

Freshly cleaned sodium metal (5.25 g, 228.3 mmol) was cut into small pieces and added to dry diethylene glycol (120 mL) under a nitrogen atmosphere. The resulting mixture was stirred at 80° C. for 15 minutes to complete formation of the sodium salt. The resulting orange solution was cooled to room temperature and a solution of Intermediate 9 (compound (XI)), 3.1 g, 18.5 mmol) in dry diethylene glycol (20 mL) was added, followed to 98.5% hydrazine (3.65 mL, 114.5 mmol). The resulting mixture was then refluxed (bath temperature 200° C.) for 50 hours. The dark orange reaction mixture was cooled to room temperature, poured into water (400 mL), and made acidic by addition of concentrated HCl. The resulting white precipitate was collected by vacuum filtration, washed with water, air-dried and taken up in diethyl ether (400 mL). The ether solution was dried over anhydrous magnesium sulfate, treated with acidic decolorizing carbon and concentrated on a rotary evaporator to yield the desired product of formula (XII) as an off-white solid (2.36 g, 84%), mp=192–195° C. (lit. mp=194–195° C., $J. Org. Chem.$ 1979, 44, 2206).

MS (–ESI) m/z=153 $(M-H)^-$.
Elemental Analysis for $C_9H_{14}O_2$
Calculated: C, 70.10; H, 9.15.
Found: C, 70.23; H, 9.32.

Example 1

(S)-N-{(2R)-2-[4-(1H-Indol-4-yl)piperazin-1-yl]propyl}-N-pyridin-2-yl-bicyclo[2.2.2]octane-2-carboxamide A solution of (S)-bicyclo[2.2.2]octane-2-carboxylic acid (Intermediate 4, 1.0 g, 6.48 mmol) and dimethylformamide (2 drops) in dichloromethane (5 mL) was treated with the dropwise addition of 2 equivalents of oxalyl chloride (2M in dichloromethane, 6.5 mL) at 0° C. under nitrogen. After stirring for two hours, the mixture was concentrated on a rotary evaporator to afford the acid chloride as a light yellow oil. A solution of (R)-1-(4-indolyl)-4-[2-methyl-2-(2-pyridinylamino)ethyl]piperazine (2.17 g, 6.48 mmol) in dichloromethane (20 mL) was treated at 0° C. with the dropwise addition of a dichloromethane solution of the freshly prepared (S)-bicyclo[2.2.2]octane-2-carboxylic acid chloride (6.48 mmol in 5 mL). After stirring for 16 hours the mixture was poured onto hexane (100 mL) to precipitate the titled compound as the monohydrochloride salt (1.77 g, 51%), mp=180–182° C.

MS (+ESI) m/z=472 (M+H)$^+$.
[α]25/D=+31.24 (c=1, MeOH)
Elemental Analysis for: $C_{29}H_{37}N_5O.1$ HCl.1.5 $H_2O$
Calculated: C, 65.09; H, 7.72; N, 13.09.
Found: C, 65.23; H, 7.41; N, 13.49.

Example 2

(R)-N-[(2R)-2-[4-(1H-Indol-4-yl)-1-piperazinyl]propyl]-N-2-pyridin-2-yl-bicyclo[2.2.2]octane-2-carboxamide A solution of (R)-bicyclo[2.2.2]octane-2-carboxylic acid-(Intermediate 5, 0.80 g, 5.19 mmol) and dimethylformamide (2 drops) in dichloromethane (5 mL) was treated with the dropwise addition of 2 equivalents of oxalyl chloride (2M in dichloromethane, 5.2 mL) at 0° C. under nitrogen. After stirring for one hour, the mixture was concentrated on a rotary evaporator to afford the acid chloride as a light yellow oil. A solution of (R)-1-(4-indolyl)-4-[2-methyl-2-(2-pyridinylamino)ethyl]piperazine (1.92 g, 5.72 mmol) in dichloromethane (25 mL) was treated at 0° C. with the dropwise addition of a dichloromethane solution of the freshly prepared (R)-bicyclo[2.2.2]octane-2-carboxylic acid chloride (5 mL). After stirring for 16 hours the mixture was poured onto hexane (100 mL) and a yellow oil formed. The oil was obtained by decanting and was partitioned between dichloromethane (100 mL) and saturated aqueous sodium bicarbonate (100 mL). The organic layer was dried over anhydrous sodium sulfate and concentrated on a rotary evaporator. The desired product was obtained as the dihydrochloride salt by treating the residue with excess HCl in ethyl acetate/diethyl ether to yield a white solid (1.64 g, 56%), mp=186–190° C.

MS (+) 472 (M+H)$^+$.
[α] 25/D=−25.45 (c=1, MeOH).
Elemental Analysis for: $C_{29}H_{37}N_5O.2$ HCl.1 $H_2O$
Calculated: C, 61.91; H, 7.35; N, 12.45.
Found: C, 62.03; H, 7.50; N, 12.31.

Example 3

N-{(2R)-2-[4-(1H-Indol-4-yl)piperazin-1-yl]propyl}-N-pyridin-2-yl-bicyclo[2.2.1]heptane-7-carboxamide A solution of bicyclo[2.2.1]heptane-7-carboxylic acid (Intermediate 6, 0.26 g, 1.86 mmol) and dimethylformamide (1 drop) in dichloromethane (7 mL) was treated with the dropwise addition of 2.2 equivalents of oxalyl chloride (2M in dichloromethane, 2.08 mL) at 0° C. under nitrogen. After stirring for three hours, the mixture was concentrated on a rotary evaporator to afford the acid chloride as a yellow oil. The freshly prepared acid chloride was dissolved in dry dichloromethane (7 mL), cooled to 0° C. and treated with a solution of and (R)-1-(4-indolyl)-4-[2-methyl-2-(2-pyridinylamino)ethyl]piperazine (0.30 g, 0.9 mmol) in dichloromethane (10 mL). The resulting mixture was stirred for 48 hours, during which time it came up to room temperature. The reaction mixture was diluted with dichloromethane (50 mL) and washed with saturated aqueous sodium bicarbonate. The organic layer was dried over anhydrous sodium sulfate and concentrated on a rotary evaporator. The desired product was isolated by chromatography on silica gel using methanol/dichloromethane and converted to the monohydrochloride salt by addition of HCl in ethyl acetate/diethyl ether (0.21 g, 46%), mp=176–179° C.

MS (+ESI) m/z=458 (M+H)$^+$.
[α] 25/D=+35.6 (c=1, MeOH).
Elemental Analysis for: $C_{28}H_{35}N_5O.1$ HCl.1 $H_2O$
Calculated: C, 65.67; H, 7.48; N, 13.68.
Found: C, 65.78; H, 7.44; N, 13.46.

Example 4

N-{(2R)-2-[4-(1H-indol-4-yl)piperazin-1-yl]propyl}-7-methyl-N-pyridin-2-yl-bicyclo[2.2.1]heptane-7-carboxamide A solution of 7-methyl-bicyclo[2.2.2]heptane-7-carboxylic acid (Intermediate 10, 0.28 g, 1.80 mmol) and dimethylformamide (1 drop) in dichloromethane (5 mL) was treated with the dropwise addition of 2.2 equivalents of oxalyl chloride (2M in dichloromethane, 2.0 mL) at 0° C. under nitrogen. The reaction was stirred overnight, during which time it came up to room temperature. The mixture was concentrated on a rotary evaporator to afford the acid chloride as a yellow oil. The freshly prepared acid chloride was dissolved in dry dichloromethane (10 mL), cooled to 0° C. and treated with a solution of (R)-1-(4-indolyl)-4-[2-methyl-2-(2-pyridinylamino)ethyl] piperazine (0.30 g, 0.9 mmol) in dichloromethane (7 mL), followed by triethylamine (0.18 g, 1.8 mmol). The resulting mixture was stirred for 96 hours, during which time it came up to room temperature. The reaction mixture was concentrated on a rotary evaporator to remove excess solvent and triethylamine. The residue was partitioned between dichloromethane (100 mL) and saturated aqueous sodium bicarbonate (75 mL). The aqueous layer was extracted with two additional portions of dichloromethane (30 mL). The combined organic layers were dried over anhydrous sodium sulfate and concentrated on a rotary evaporator. The desired product was isolated by chromatography on silica gel using methanol/dichloromethane and converted to the monohydrochloride salt by addition of HCl in ethyl acetate/diethyl ether (0.36 g, 76%), mp=236–238° C.

MS (+ESI) m/z=472 (M+H)$^+$.
[α] 25/D+37.1 (c=1, MeOH).
Elemental Analysis for: $C_{29}H_{37}N_5O.1$ HCl.1 $H_2O$
Calculated: C, 66.20; H, 7.66; N, 13.31.
Found: C, 65.95; H, 7.51; N, 13.26.

Serotonin 5-HT$_{1A}$ Binding Profile

Affinity for the serotonin 5-HT$_{1A}$ receptor was established by assaying the test compound's ability to displace [$^3$H]8-

OH-DPAT from its binding site on the receptor complex in CHO cells stably transfected with the human 5-HT$_{1A}$ receptor following the procedure described by Dunlop et al., *J. PharmacoL ToxicoL Methods* 1998, 40, 47. The compounds of this invention displayed high affinity for the 5-HT$_{1A}$ receptor, as shown in Table 1.

In vitro Functional Activity

The compounds of formula (1) displayed 5-HT$_{1A}$ antagonist activity, as measured by the test compound's ability to antagonize the ability of the 5-HT$_{1A}$ full agonist 8-OH-DPAT to inhibit forskolin-stimulated cyclic-AMP turnover in CHO cells stably transfected with the human 5-HT$_{1A}$ receptor following the procedure described by Dunlop et al., *J. Pharmacol. Toxicol. Methods* 1998, 40, 47.

TABLE 1

| Compound | 5-HT$_{1A}$ Ki (nM) | cAMP IC$_{50}$ (nM) |
| --- | --- | --- |
| Example 1 | 0.68 | 4.1 |
| Example 2 | 0.69 | 2.2 |
| Example 3 | 0.98 | 74.5 |
| Example 4 | 0.45 | 6.7 |

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of formula (I):

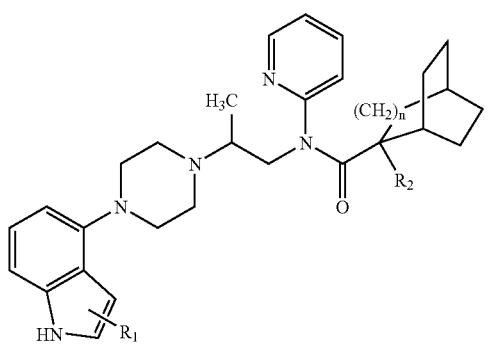

(I)

or a stereoisomer, N-oxide or pharmaceutically-acceptable salt thereof;
wherein:
R$_1$ is H, halo or alkyl;
R$_2$ is H or lower alkyl; and
n is 0 or 1.

2. A compound according to claim 1,
wherein:
R$_2$ is H or methyl.

3. A compound according to claim 2,
wherein:
R$_1$ is H or alkyl; and
n is 1.

4. A compound according to claim 1 selected from the group consisting of:
(S)-N-{(2R)-2-[4-(1H-indol-4-yl)piperazin-1-yl]propyl}-N-pyridin-2-ylbicyclo[2.2.2]octane-2-carboxamide;
(R)-N-{(2R)-2-[4-(1H-indol-4-yl)piperazin-1-yl]propyl}-N-pyridin-2-ylbicyclo[2.2.2]octane-2-carboxamide;
N-{(2R)-2-[4-(1H-indol-4-yl)piperazin-1-yl]propyl}-7-methyl-N-pyridin-2-yl-bicyclo[2.2.1]heptane-7-carboxamide;
N-{(2R)-2-[4-(1H-indol-4-yl)piperazin-1-yl]propyl}-7-methyl-N-pyridin-2-yl-bicyclo[2.2.1]heptane-7-carboxamide; and
N-oxides and pharmaceutically-acceptable salts thereof.

5. A compound according to claim 4 selected from the group consisting of:
(S)-N-{(2R)-2-[4-(1H-indol-4-yl)piperazin-1-yl]propyl}-N-pyridin-2-ylbicyclo[2.2.2]octane-2-carboxamide;
(R)-N-{(2R)-2-[4-(1H-indol-4-yl)piperazin-1-yl]propyl}-N-pyridin-2-ylbicyclo[2.2.2]octane-2-carboxamide; and
N-oxides and pharmaceutically-acceptable salts thereof.

6. A composition, comprising:
the compound of claim 1; and
one or more pharmaceutically-acceptable carriers.

7. A composition according to claim 6, further comprising at least one of selective serotonin reuptake inhibitor.

8. A method of treating a patient suspected to suffer from a central nervous system (CNS) disorder,
comprising the step of administering to the patient an effective amount of the compound of claim 1;
wherein said central nervous system disorder is a disorder selected from the group consisting of anxiety, depression, cognitive deficits resulting from Alzheimer's disease, schizophrenia, and combinations thereof.

9. A method for treating anxiety in a patient in need thereof, comprising the step of:
administering to the patient an effective amount of the compound of claim 1.

10. A method for treating depression in a patient in need thereof, comprising the step of:
administering to the patient an effective amount of the compound of claim 1.

11. A method for treating a cognitive deficit resulting from Alzheimer's disease in a patient in need thereof, comprising the step of:
administering to the patient an effective amount of the compound of claim 1.

12. A method for treating schizophrenia in a patient in need thereof, comprising the step of:
administering to the patient an effective amount of the compound of claim 1.

13. A method for enhancing the onset of action or potency of antidepressant activity of selective serotonin reuptake inhibitors in a patient in need thereof, comprising the step of:
administering to the patient
an effective amount of at least one compound of claim 1; and
an effective amount of at least one of selective serotonin reuptake inhibitor.

14. A method for treating withdrawal symptoms induced by cessation of smoking or use of nicotine-containing products in a patient in need thereof, comprising the step of:
administering to the patient an effective amount of the compound of claim 1.

* * * * *